(12) United States Patent
Garrett et al.

(10) Patent No.: US 9,387,337 B2
(45) Date of Patent: *Jul. 12, 2016

(54) ENERGY DELIVERY APPARATUS AND METHOD

(71) Applicant: ZOLL Medical Corporation, Chelmsford, MA (US)

(72) Inventors: Michael C. Garrett, Wilmette, IL (US); Robert Larson, Northfield, IL (US); Jerry Bazata, Buffalo Grove, IL (US); Dean L. Milani, Antioch, IL (US); William J. Smirles, Deerfield, IL (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,260

(22) Filed: Mar. 6, 2015

(65) Prior Publication Data

US 2015/0174421 A1    Jun. 25, 2015

Related U.S. Application Data

(63) Continuation of application No. 14/064,533, filed on Oct. 28, 2013, now Pat. No. 8,983,599, which is a continuation of application No. 13/623,504, filed on Sep. 20, 2012, now abandoned, which is a continuation of application No. 12/692,809, filed on Jan. 25, 2010, now Pat. No. 8,301,245, which is a continuation of (Continued)

(51) Int. Cl.
*A61N 1/00* (2006.01)
*A61N 1/39* (2006.01)

(52) U.S. Cl.
CPC ............... *A61N 1/3987* (2013.01); *A61N 1/39* (2013.01); *A61N 1/3975* (2013.01); *A61N 1/3912* (2013.01); *A61N 1/3931* (2013.01)

(58) Field of Classification Search
CPC ..... A61N 1/39; A61N 1/3912; A61N 1/3931; A61N 1/3975; A61N 1/3987
See application file for complete search history.

(56) References Cited

U.S. PATENT DOCUMENTS

| 3,787,767 A | 1/1974 | Hammer et al. |
|---|---|---|
| 4,077,413 A | 3/1978 | Partridge |
| 5,443,490 A | 8/1995 | Flugstad |

(Continued)

OTHER PUBLICATIONS

An Information Disclosure Statement (filed in the grand parent application on Jan. 25, 2010).

*Primary Examiner* — George Manuel
(74) *Attorney, Agent, or Firm* — Fish & Richardson P.C.

(57) ABSTRACT

There is provided an energy delivery device comprising a storage device, a discharge circuit and a disarm circuit. The discharge circuit comprises a switch electrically connected to the storage device, and is selectively operable to deliver energy from the storage device to a load, e.g., a patient needing defibrillation, preferably in a multiphasic waveform. The disarm circuit comprises the switch. Preferably, the discharge circuit comprises an H-bridge circuit. There are also provided delivery devices: which comprise a shoot-through elimination circuit; which include housing elements which, when assembled, cause electrical connection between respective components; which include a housing having a small volume and an energy storage device having a large capacitance; which comprise a shunt circuit which, when activated, prevents switching of a switch. There are also provided methods of assembly and disassembly of an energy delivery unit and methods of delivering energy to a load.

13 Claims, 12 Drawing Sheets

Related U.S. Application Data application No. 10/876,782, filed on Jun. 25, 2004, now Pat. No. 7,680,533.

(60) Provisional application No. 60/482,292, filed on Jun. 25, 2003.

(56) References Cited

U.S. PATENT DOCUMENTS

| | | |
|---|---|---|
| 5,873,893 A | 2/1999 | Sullivan et al. |
| 6,029,085 A | 2/2000 | Olson et al. |
| 6,041,254 A | 3/2000 | Sullivan et al. |
| 6,253,105 B1 * | 6/2001 | Leyde ................... 607/5 |
| 6,392,364 B1 | 5/2002 | Yamamoto et al. |
| 6,907,285 B2 | 6/2005 | Denker et al. |
| 7,570,994 B2 | 8/2009 | Tamura et al. |
| 7,680,533 B2 | 3/2010 | Garrett et al. |
| 8,301,245 B2 | 10/2012 | Garrett et al. |
| 2003/0055460 A1 | 3/2003 | Owen et al. |
| 2005/0187583 A1 | 8/2005 | Garrett et al. |
| 2010/0174331 A1 | 7/2010 | Garrett et al. |

* cited by examiner

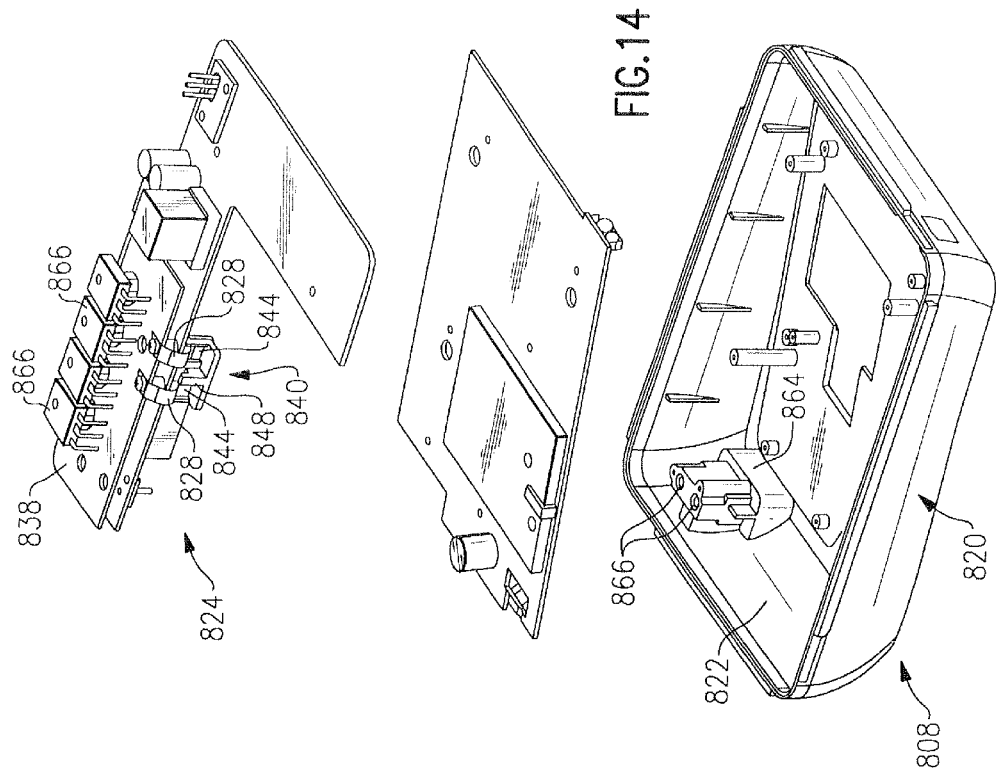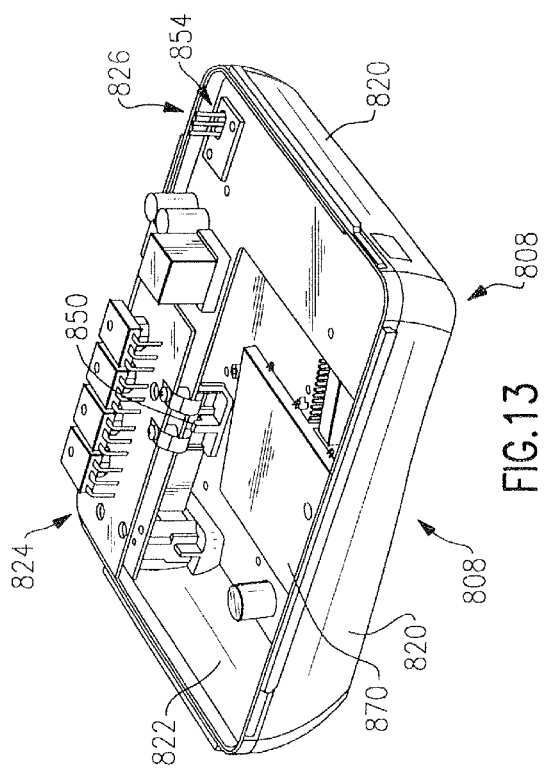

ENERGY DELIVERY APPARATUS AND METHOD

CROSS-REFERENCE TO RELATED APPLICATION

This application is a continuation of and claims priority under 35 USC 120 to U.S. application Ser. No. 14/064,533 filed Oct. 28, 2013 (U.S. Pat. No. 8,983,599 to be issued Mar. 27, 2015), which is a continuation application of U.S. application Ser. No. 13/623,504 filed Sep. 20, 2012 (now abandoned), which is a continuation application of U.S. application Ser. No. 12/692,809 filed Jan. 25, 2010 (now U.S. Pat. No. 8,301,245), which is a continuation application of U.S. application Ser. No. 10/876,782, filed Jun. 25, 2004 (now U.S. Pat. No. 7,680,533) and claims the benefit of U.S. Provisional Patent Application No. 60/482,292, filed Jun. 25, 2003, the entireties of which are incorporated herein by reference.

FIELD OF THE INVENTION

The invention relates to an energy delivery apparatus and method and, more particularly, to circuits for an energy delivery apparatus, and methods of assembly and disassembly.

BACKGROUND OF THE INVENTION

Cardiotherapeutic defibrillators, once used only by trained medical personnel, are now being made available for use by the general population, including individuals having little or no training. The defibrillators contemplated for general use are of the automatic external type and include on-board real time diagnostic capability to intervene or otherwise control the defibrillator therapy being administered. In general, the defibrillators deliver a relatively high voltage, low energy pulse or series of pulses to a patient suffering cardiac arrhythmias, such as ventricular fibrillation. The power supply relied upon to deliver the defibrillation therapy typically comprises one or more batteries carried on board the defibrillator unit or an electrical power utility supplying power to a building, for example. Because of the nature of the electrical therapy required, it is generally not possible in a practical device to supply the therapeutic energy upon instantaneous demand, by drawing from the power source. Instead, energy from the power source is typically accumulated over a period of time in one or more defibrillator capacitors that are later discharged to deliver the desired defibrillation therapy. It is usually critical that the defibrillation therapy be delivered as quickly as possible, given the nature of the medical threat encountered.

Practical defibrillation equipment must also be capable of rapid discharging (or disarming) in order to prepare for a controlled sequence of operation. Discharging may be required, for example, when a portable defibrillation unit is to be packed away for return transport to a hospital or dispatch office. At other times, discharging of a defibrillator capacitor bank is required when the therapeutic action is to be performed at a lower capacitor voltage. For example, patients of different ages require adjustments in the defibrillation voltage applied, with younger patients requiring lesser voltage levels. A patient's age may, for example, be indirectly conveyed to the defibrillation equipment by the choice of defibrillator paddles connected to the defibrillation equipment. Currently, sophisticated automated defibrillation units exist in the art that are capable of determining the defibrillation voltage required based on the size of the paddles selected. These units then automatically discharge the capacitor to the appropriate voltage setting. Alternatively, these units may require operator intervention to confirm the voltage setting. In any case, excess voltage stored in the capacitor is discharged to achieve the correct voltage level.

In other types of defibrillation equipment in common use today, an operator is required to manually select the defibrillation voltage, either directly or indirectly through settings bearing various legends. An inexperienced or untrained field operator could, by cycling the defibrillator voltage setting, cause the voltage reduction circuit undue stress. Typically, the greatest stress is borne by a discharge resistor or a like dissipative disarm device which can become extremely warm during this type of unusual operating condition. Unusually heavy use, even though otherwise proper, could also cause unacceptable stress on a defibrillator disarm circuit.

Previous disarm circuits used for discharging a capacitor bank have been constructed utilizing a separate current path outside of the energy switching components. This current path requires a high voltage switch, separate from the energy switching components to control the current flow through a discharging device. Alternatively, to avoid high voltage components, several smaller low voltage switches can be placed in series. In either case, a distinct and separate switch or switches in addition to those used for energy switching functions are required, undesirably increasing the component count and space requirements for the defibrillator unit.

For example, FIG. 1 shows a discharge circuit utilizing a temperature controller 109 that monitors the temperature, allowing a controller 108 to modulate the current through discharge component 103 by on-off modulation of a high voltage switch 105. However, this device requires the use of the high voltage switch 105, in addition to the high voltage switches present in the energy delivery circuit 102, thereby increasing the part count and space requirements of the defibrillator unit.

In addition, previous defibrillator output circuits fail to account for shoot-through current that can be generated in an energy delivery circuit configured as an H-Bridge, causing undesirable consequences. For example, referring to FIG. 2, a prior art defibrillator circuit is shown capable of delivering an energy pulse to a patient load 217. After capacitor 201 is charged to the desired voltage, resistors 215 and 216 hold the patient connections to a voltage potential that represents the positive potential across capacitor 201 when switches 211, 212 and 213 are in the off state. In this state, no current flows through the patient load 217. When current flow is required, switches 212 and 213 are rapidly turned on. The voltage to current transfer ratio or gain determines the gate voltage required to turn on the switches 212 and 213. The gain of the switch is a variable parameter and may not be tightly controlled. The rapid turn-on of switch 213 causes a large negative dv/dt (change in voltage over time) to be present at the emitter of switch 211. The gate of switch 211 should follow the negative voltage swing with current flowing through resistor 233 such that a potential difference between the gate and emitter of switch 211 remains below the turn-on threshold. However, parasitic capacitances, represented by capacitors 218 and 219, are formed by the internal capacitances of the switch itself, other component capacitances, and the electrical connections within the board layout. These parasitic capacitances form a capacitive voltage divider that can cause the voltage at the gate of switch 211 to build-up, thereby causing a partial or full nuisance turn-on of switch 211 while switch 213 is conducting. As can be seen in FIG. 2, if switches 211 and 213 are both conducting simultaneously, a direct path to ground is formed allowing a shoot-through current pulse to flow from capacitor 201. This current pulse can be of a large magnitude and possibly cause damage to switches 211 and 213, permanently damaging the defibrillator. The shoot-through turn on is mainly caused by the Miller capacitances of switch 211. These capacitances are hard to control, and are only approximated on the data sheets of the components.

In external defibrillator units, one common disadvantage is in their size. As these units are meant to be portable so that they can be easily transported by the end user during emergency situations, large and bulky units are undesirable. On the other hand, the compact size that is desired generally competes with the need to deliver relatively high energy levels to a patient for effective defibrillation. In smaller size units, the capacitors utilized for the energy storage device generally have to be sized smaller as well. The problem this creates is that the voltage developed in the unit has to be higher to deliver the required energy level to a patient, particularly for multiphasic energy pulses so that the energy is not exhausted prior to the desired termination of the delivered energy. To this end, the width or duration of the energy pulse generally has to be made shorter than is desirable in prior small defibrillator units.

SUMMARY OF THE INVENTION

It is an object of the present invention to overcome the problems of the prior art, and/or to eliminate limitations of the prior art, by providing energy delivery devices and methods that reduce the overall size of the energy delivery unit by integration of discharge circuit and disarm circuit components, and/or in which electrical connection between at least one pair of components is made when a housing of the apparatus is assembled and not made when the housing is disassembled. It is a further object of the present invention to overcome the problems of the prior art, and/or to eliminate limitations of the prior art, by providing energy delivery devices and methods that include a shoot-through elimination circuit.

In one aspect of the invention, there is provided an energy delivery device which comprises an energy storage device, an energy discharge circuit which comprises a first switch electrically connected to the energy storage device and a disarm circuit which comprises the first switch. The energy discharge circuit is selectively operable to deliver to a load energy from the energy storage device in a form of at least one energy pulse. The disarm circuit is selectively operable to reduce energy in the storage device. Preferably, the load is a human patient.

In the prior art circuit depicted in FIG. 2, the resistance of the resistor 215 was 100,000 ohms or higher. Due to this high resistance, the circuit cannot remove energy from the energy storage device rapidly enough to be characterized as including the functionality of a disarm circuit.

In a preferred embodiment in accordance with the present invention, the disarm circuit comprises an energy dissipater device that is electrically connected in series with the energy discharge circuit including the first switch.

In another preferred embodiment in accordance with the present invention, the energy discharge circuit further comprises a controller and a control circuit for the first switch, and the controller selectively causes delivery of an energy pulse to the load or energy reduction of the storage device. The controller preferably comprises a controller power source, and the disarm circuit is automatically operable to reduce energy in the energy storage device when the controller power source is not powering the controller. The controller preferably automatically causes the disarm circuit to reduce energy in the energy storage device when a level of stored energy in the energy storage device exceeds a predetermined energy level.

In another preferred embodiment in accordance with the present invention, the energy discharge circuit comprises a plurality of delivery switches which are operable to deliver the at least one energy pulse, and the first switch is one of the delivery switches. Preferably, the energy discharge circuit comprises an H-bridge circuit which comprises four delivery switches.

In another preferred embodiment in accordance with the present invention, the energy discharge circuit is configured to provide a multiphasic waveform for the at least one energy pulse. Preferably, the multiphasic waveform is a truncated exponential multiphasic waveform.

The energy storage device, the discharge circuit and the disarm circuit are preferably positioned within a housing having a volume of not more than about 130 cubic inches. In a preferred embodiment in accordance with the present invention, the housing has a box-like configuration having a length dimension of about eight inches, a width dimension of about seven inches, and a height dimension in a range of from about two inches to about three inches. Preferably, the height dimension of the housing varies from front to back so as to be higher toward the rear at about three inches and lower toward the front at about two inches.

In a preferred embodiment in accordance with the present invention, the energy discharge circuit comprises at least first and second delivery switches and at least first and second terminals for connection to the load, and the disarm circuit includes at least one disarm resistor having first and second ends and the second delivery switch. In this embodiment, an input end of the first delivery switch is electrically connected to the energy storage device, an output end of the first delivery switch is electrically connected to the first terminal, the first end of the disarm resistor is electrically connected to the energy storage device, the second end of the disarm resistor is electrically connected to the input end of the second delivery switch, the output end of the second delivery switch is electrically connected to ground, the first terminal is electrically connected to the output end of the first delivery switch, and the second terminal is electrically connected to the input end of the second delivery switch. The energy discharge circuit of this embodiment preferably further includes a controller and a control circuit and the first and second delivery switches are preferably each independently controlled by the controller. The energy delivery device of this embodiment preferably further comprises a third delivery switch and a fourth delivery switch, and an input end of the third delivery switch is electrically connected to the energy storage device, an output end of the third delivery switch is electrically connected to the second terminal, an input end of the fourth delivery switch is electrically connected to the second terminal, and an output end of the fourth delivery switch is electrically connected to ground.

Preferably, the energy delivery device of this embodiment further comprises a controller and a control circuit, where the controller has a controller output, a first disarm circuit resistor having first and second ends, a first disarm circuit switch having an input end and an output end, at least one turn-on circuit having an input end and an output end, a second disarm circuit resistor having first and second ends, and a second disarm circuit switch having an input end and an output end; and, the first disarm circuit resistor first end is electrically connected to the energy storage device; the first disarm circuit resistor second end is electrically connected to each of: the first disarm circuit switch input end, the turn-on circuit input end, the second disarm circuit resistor first end and the second delivery switch, whereby current through the first disarm circuit resistor controls the second delivery switch; the first disarm circuit switch output end and the turn-on circuit output end are electrically connected to ground; the second disarm circuit resistor output end is electrically connected to the second disarm circuit switch input end; the second disarm circuit switch output end is electrically connected to ground; the controller output is electrically connected to the first disarm circuit switch and the second disarm circuit switch to control the first disarm circuit switch and the second disarm circuit6 switch; whereby, when the controller is not receiving a minimum amount of power, the disarm circuit reduces energy in the energy storage device.

In accordance with another aspect of the invention, there is provided an energy delivery device for delivering an energy pulse to a load, which comprises an energy storage device, an energy discharge circuit which comprises a plurality of delivery switches, a controller and a shoot-through elimination circuit. The delivery switches are selectively operable to deliver to a load energy from the energy storage device in a form of at least one energy pulse in a waveform. Each of the delivery switches has an on condition and an off condition for enabling delivery of energy in different stages of the waveform. The controller shifts at least a first switch of the plurality of delivery switches to an on condition and at least a second switch of the plurality of delivery switches to an off condition for generating one waveform phase and shifts at least the second switch to an on condition and at least the first switch to an off condition for generating another waveform phase. The shoot-through elimination circuit is operable to keep the first switch in an off condition when the second switch is shifted to an on condition by operation of the controller. Preferably, the load is a human patient. Typically, the switches include parasitic components, and preferably the shoot-through elimination circuit comprises a shunting circuit that avoids causing the first switch to be shifted to an on condition because of the parasitic components with shifting of the second switch to an on condition. Preferably, the shoot-through elimination circuit comprises a clamping element to avoid voltage build-up in the first switch.

In a preferred embodiment, the discharge circuit is configured as an H-bridge circuit, and the plurality of switches comprises a pair of high switches and a pair of low switches, with the first switch being one of the high switches.

In accordance with another aspect of the invention, there is provided an energy delivery apparatus, which comprises a housing, an energy storage device and a discharge circuit. The housing comprises a first housing element and a second housing element, and it has an assembled orientation in which the first housing element and the second housing element are engaged with each other. The energy storage device and the discharge circuit are positioned in the housing. The discharge circuit is selectively operable to deliver to a load energy from the energy storage device in a form of at least one energy pulse. The energy storage device and the discharge circuit together include a plurality of electrical components. At least a first of the electrical components is mounted on the first housing element, at least a second of the electrical components is mounted on the second housing element. The first electrical component and the second electrical component are electrically connected to each other (without wiring extending between them) when the housing is in the assembled orientation and they are not electrically connected to each other when the housing is not in the assembled orientation. Preferably, the load is a human patient. The energy storage device is preferably maximized in rating to allow voltage for the discharge circuit to be minimized. Preferably, the housing has a volume of not more than about 140 cubic inches and the rating of the energy storage device is at least about 250 microfarads. Preferably, the discharge circuit comprises an H-bridge circuit that generates multiphasic waveforms. Preferably, the maximized rating of the energy storage device allows for a voltage of at least about 1300 volts to be developed for the discharge circuit. Preferably, a wireless detachable electrical connection is provided between the discharge circuit and the energy storage device. Preferably, the discharge circuit is provided on the first housing element and the energy storage device is provided on the second housing element, and the discharge circuit and the energy storage device are slidably connectable for electrically connecting the discharge circuit and the energy storage device in engaging the first and second housing elements with each other.

In a preferred embodiment according to this aspect of the present invention, the discharge circuit and the energy storage device include electrical contacts and cam surfaces that engage each other when the first and second housing elements are engaged with each other to provide electrical connection between the discharge circuit and the energy storage device.

In this aspect of the present invention, the energy delivery apparatus preferably further comprises a disarm circuit which selectively reduces energy stored in the energy storage device, the disarm circuit and the discharge circuit sharing at least one electronic component.

In accordance with yet another aspect of the invention, there is provided an energy delivery apparatus which comprises a housing having a volume of not greater than about 140 cubic inches, a discharge circuit positioned in the housing for selectively delivering an energy pulse to a load and an energy storage device in the housing having a capacitance of at least about 250 microfarads. Preferably, the load is a human patient.

In accordance with this aspect of the present invention, preferably, a wireless detachable electrical connection is provided between the discharge circuit and the energy storage device.

In accordance with this aspect of the present invention, preferably, the housing comprises a first housing element and a second housing element, the housing has an assembled orientation in which the first housing element and the second housing element are engaged with each other, the discharge circuit is provided on the first housing element and the energy storage device is provided on the second housing element, and the discharge circuit and the energy storage device are slidably connectable for electrically connecting the discharge circuit and the energy storage device in engaging the first and second housing elements with each other. Preferably, the discharge circuit and the energy storage device include electrical contacts and cam surfaces that engage each other when the first and second housing elements are engaged with each other to provide electrical connection between the discharge circuit and the energy storage device. Preferably, at least one of the contacts has a resilient configuration for camming against and biasing into engagement with at least another one of the contacts.

In accordance with this aspect of the present invention, preferably, the discharge circuit comprises an H-bridge circuit for generating multi-phasic energy waveforms, and the energy storage device generates at least about 1300 volts of power for the discharge circuit to provide the waveforms.

In accordance with another aspect of the invention, there is provided a method of assembly and disassembly of an energy delivery unit. This method comprises moving a first housing half relative to a second housing half in order to engage the first housing half with the second half, an energy storage device being positioned in the housing and a discharge circuit being positioned in the housing. The discharge circuit is selectively operable to deliver to a load energy from the energy storage device in a form of at least one energy pulse. The energy storage device and the discharge circuit together include a plurality of electrical components. At least a first of the electrical components is mounted on the first housing element and at least a second of the electrical components is mounted on the second housing element. The discharge circuit and the energy storage device are changed from being electrically disconnected from one another to being electrically connected to one another as a result of the moving the first housing half relative to the second housing half. Preferably, the discharge circuit and the energy storage device are respectively positioned on different housing halves.

In accordance with this aspect of the present invention, preferably, the discharge circuit and the energy storage device are slidably connectable for electrically connecting the discharge circuit and the energy storage device in engaging the first and second housing elements with each other.

In accordance with this aspect of the present invention, preferably, the discharge circuit and the energy storage device include electrical contacts and cam surfaces that engage each other when the first and second housing elements are engaged with each other to provide electrical connection between the discharge circuit and the energy storage device.

In accordance with yet another aspect of the invention, there is provided an energy delivery device comprising an energy storage device, a discharge device operably coupled to the energy storage device and a shunt circuit. The discharge device comprises a switch having electrodes across which a voltage can develop. The shunt circuit is responsive to the voltage across the electrodes and operatively coupled to a control input of the switch, such that the voltage, when present, causes the shunt circuit to prevent the voltage from causing switching of the switch. Preferably, the shunt circuit comprises a voltage divider operably coupled to the control input of the switch. Preferably, the voltage divider comprises at least a first capacitor. Preferably, the voltage divider further comprises at least a second capacitor. The shunt circuit preferably further comprises a second switch that is configured and arranged to become active in response to the voltage and to shunt the voltage away from the control input of the switch when active.

In accordance with another aspect of the present invention, there is provided a method of delivering energy to a load, comprising delivering at least one energy pulse from an energy storage device through an energy discharge circuit. The energy discharge circuit comprises a first switch electrically connected to the energy storage device, the first switch also being part of a disarm circuit which is selectively operable to reduce energy in the storage device. Preferably, the load is a human patient. Preferably, the at least one energy pulse is delivered in a multiphasic waveform. In a particularly preferred aspect, the at least one energy pulse is delivered in a truncated exponential multiphasic waveform.

BRIEF DESCRIPTION OF THE DRAWINGS

FIG. 13 is a perspective view of the upper housing member assembly of the embodiment depicted in FIG. 11, inverted to show the circuit boards mounted therein;
FIG. 14 is an exploded, perspective view of the upper housing member and circuit boards of the embodiment depicted in FIG. 13.

DETAILED DESCRIPTION OF THE INVENTION

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are typically not depicted in order to facilitate a less obstructed view of these various embodiments of the present invention.

A statement herein that two components in a device are "electrically connected," means that there are no components electrically between the components, the insertion of which materially affect the function or functions provided by the device. For example, two components can be referred to as being electrically connected, even though they may have a small resistor between them which does not materially affect the function or functions provided by the device (indeed, a wire connecting two components can be thought of as a small resistor); likewise, two components can be referred to as being electrically connected, even though they may have an additional electrical component between them which allows the device to perform an additional function, while not materially affecting the function or functions provided by a device which is identical except for not including the additional component; similarly, two components which are directly connected to each other, or which are directly connected to opposite ends of a wire or a trace on a circuit board, are electrically connected.

Figure 3:
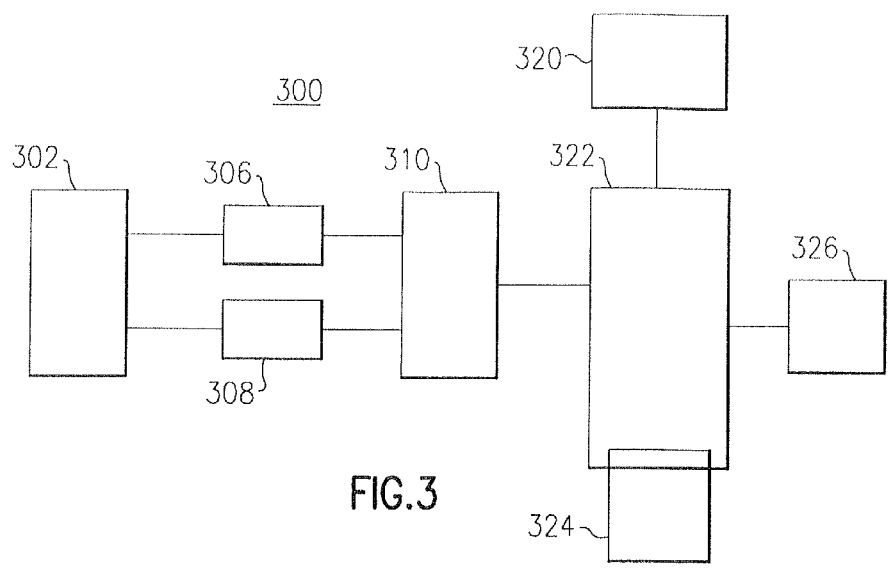
FIG. 3 is a block diagram of an embodiment of a defibrillator circuit in accordance with the present invention.

FIG. 3 depicts a preferred embodiment according to the present invention. Referring to FIG. 3, an energy delivery device 300 in accordance with the present invention is illustrated. Energy delivery device 300 includes controller 302, transformers 306 and 308, shoot-through elimination circuit 310, energy delivery circuit 322, disarm circuit 324 (which shares at least one component with the energy delivery circuit 322), energy storage device 320, and load 326. Controller 302 is electrically coupled to transformers 306 and 308. Transformers 306 and 308 are electrically coupled to shoot-through elimination circuit 310. Shoot-through elimination circuit 310 is electrically coupled to energy delivery circuit 322. Energy delivery circuit 322 is electrically coupled to energy storage device 320 and load 326. Disarm circuit 324 is electrically coupled to, and shares at least one component with, energy delivery circuit 322.

The various features included in the above-described device can be selectively implemented in an energy delivery device, although it is preferred to include each as described hereinafter. Accordingly, other forms of an energy delivery device 300 may omit one of the integrated disarm circuit 324 or shoot-through elimination circuit 310 depending on the requirements or needs for a particular energy delivery device.

Energy delivery circuit 322 preferably includes a plurality of high voltage switches, such as Insulated Gate Bipolar Transistors (IGBTs), for example. However, other types of high energy switching devices, such as Field Effect Transistors (FETs), transistors, or Metal-Oxide Semiconductor Field-Effect Transistors MOSFETs may be used as long as they are capable of operating in high voltage conditions; for example with 1600 volts as measured across the device.

In one embodiment, the switches of energy delivery circuit 322 are IGBTs arranged in an H-bridge configuration to generate a multiphasic waveform, and more particularly, a truncated exponential multiphasic waveform to load 326. When the switches of the energy delivery circuit are IGBTs, the drain represents the input to the switch and the source represents the output from the switch. The gain represents the control input of the switch.

Integrated disarm circuit 324 includes an energy dissipater device, for example, a resistor, that is connected in series with other elements of disarm circuit 324. As discussed previously, disarm circuit 324 shares at least a switch with discharge circuit 322. By sharing one or more components between energy delivery circuit 322 and disarm circuit 324, the number of components in disarm circuit 324 is minimized. In addition to being under command of controller 302, disarm circuit 322 is automatically operated to reduce the energy level in energy storage device 320 when controller 302 is not powered by a power source.

Controller 302 is any type of processing device that is capable of executing computer instructions stored in a memory. In a preferred embodiment, controller 302 is a microprocessor that is powered by a separate power source, such as a battery. Controller 302 provides commands to energy delivery circuit 322 to deliver energy pulses to load 326. In this manner, controller 302 causes energy reduction in storage device 320. Controller 302 further monitors the energy level of energy storage device 320 to ensure that the energy level does not exceed a predetermined threshold. For example, if the energy level in energy storage device 322 reaches or exceeds a predetermined energy level, controller 302 provides commands to integrated disarm circuit 324 to reduce the energy level (i.e., other than to load 326).

Energy storage device 320 can be in the form of a capacitive device such as a bank of capacitors. In a preferred embodiment, energy storage device 320 is a bank of capacitors with a capacitance value of greater than 300 microfarads.

Transformers 306 and 308 rectify the signals from controller 302 prior to delivery to energy delivery circuit 322. Transformers 306 and 308 further provide isolation between controller 302 and the high voltage levels within energy delivery circuit 322.

Shoot-through elimination circuit 310 is provided to substantially reduce or eliminate the shoot-through current associated with the inadvertent turn-on of switches within energy delivery circuit 322 as previously discussed. In a preferred embodiment, shoot-through elimination circuit 310 controls shoot-through current by shunting the gate voltage buildup on the gate of a switch within the energy delivery circuit 322. As will be discussed more fully hereinafter, shoot-through elimination circuit 310 controls the voltage at the gate of a switch with a minimum number of components, allowing reduced size, decreased part count and increased reliability of the device.

Figure 4:
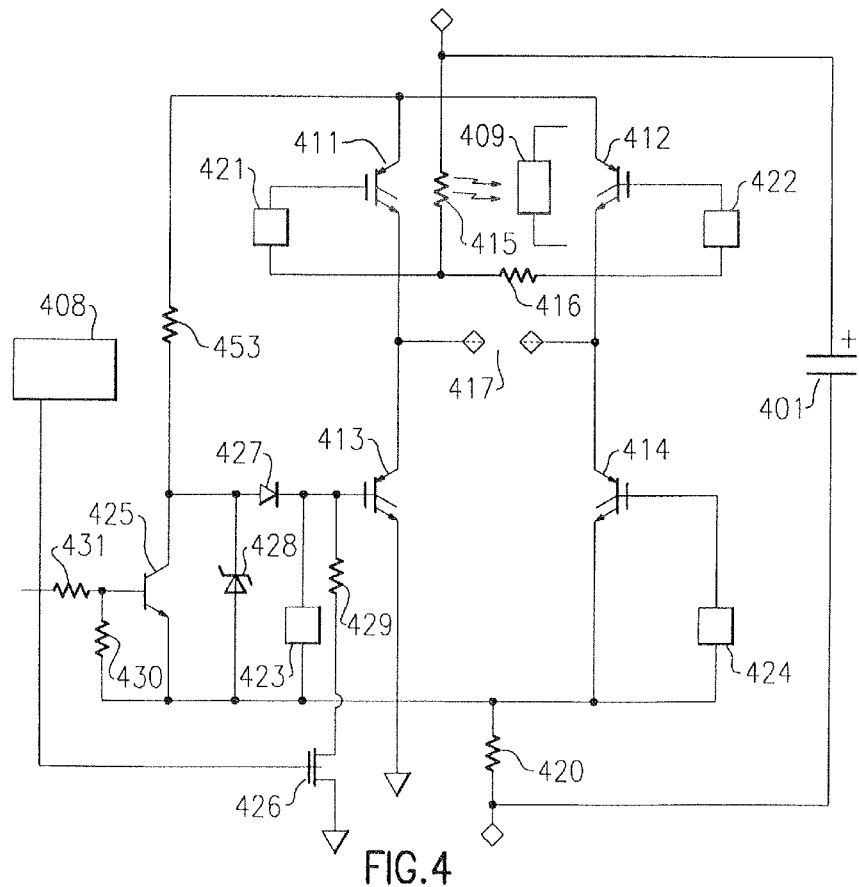
FIG. 4 is a schematic diagram showing embodiments of energy delivery and disarm circuits in accordance with the present invention.

Referring now to FIG. 4, a multiphasic defibrillator circuit including an energy delivery circuit in an H-Bridge configuration and including the disarm circuit of the present invention is shown. The energy delivery circuit includes energy storage device 401, controller 408, switches 411, 412, 413 and 414, resistors 415, 416 and 420, turn-on circuits 421, 422, 423 and 424 and load terminals 417. Energy storage device 401 is preferably in the form of a capacitive storage device such as a capacitor or bank of capacitors. In the present embodiment, energy storage device is a capacitor or bank of capacitors with a combined capacitance value greater than 300 microfarads. Switches 411, 412, 413 and 414 are preferably high voltage switches capable of operating with 1600 volts as measured across the device. In the present embodiment, switches 411, 412, 413, and 414 are IGBTs.

The disarm circuit as shown in FIG. 4 includes switches 413, 425 and 426, resistors 415, 420, 429, 430, 431 and 453, diode 427, zener diode 428 and temperature monitor 409. In the present embodiment, switch 425 is an npn transistor. However, switch 425 can be any switch that will operate in low voltages such as an IGBT, Field-Effect Transistor (FET), npn Transistor or Metal-Oxide Semiconductor Field-Effect Transistor (MOSFET). When switch 425 is an npn transistor, the collector represents the input to the switch and the emitter represents the output from the switch. The base represents the control input of the switch. Switch 426 may be any suitable switching device such as a FET, for example. When switch 426 is a FET, the drain represents the input to the switch, the source represents the output from the switch and the gate represents the control input of the switch. Diode 427 is any suitable diode that allows the drive signal from turn-on circuit 423 to be applied to the gate of switch 413 when switch 425 is in the on state. In the present embodiment, diode 427 is an IN4148. Zener diode 428 is any suitable zener diode or similar device used to limit voltage achieved by current flowing through resistor 453 biasing the gate of switch 413. Temperature monitor 409 can be any device capable of sensing the temperature of a circuit component and modifying an electrical parameter accordingly, which is readable by controller 408.

As can be seen, at least switch 413 and resistor 415 are shared between the energy delivery circuit and the disarm circuit so as to provide efficiencies both in part count reduction and space requirements for the electronic components of the energy delivery device in accordance with the present invention.

With regard to the connections of the energy delivery circuit, the drains of switches 412 and 411 are electrically connected to the positive terminal of energy storage device 401, a first side of resistor 415 and to each other. The source of switch 411 is electrically connected to a second side of resistor 415, a first side of resistor 416, a first terminal of turn-on circuit 421, a first side of load terminals 417 and the drain of switch 413. The source of switch 412 is electrically connected to a second side of resistor 416, a first terminal of turn-on circuit 422, a second side of load terminals 417 and the drain of switch 414. The gate of switch 411 is electrically connected to a second terminal of turn-on circuit 421 and the gate of switch 412 is electrically connected to a second terminal of turn-on circuit 422. The source of switch 414 is electrically connected to a first terminal of turn-on circuit 424, a first side of resistor 420 and to ground. The gate of switch 414 is electrically connected to a second terminal of turn-on circuit 424. The source of switch 413 is electrically connected to a first terminal of turn-on circuit 423, a first side of resistor 420 and to ground. The gate of switch 413 is electrically connected to a second terminal of turn-on circuit 423. The positive terminal of energy storage device 401 is electrically connected to the drains of switches 411 and 412 and the first side of resistor 415. The negative terminal of energy storage device 401 is electrically connected to a second side of resistor 420. Controller 408 is also electrically connected to the second side of resistor 420, although this connection is not shown for the sake of clarity. Turn-on circuits 421, 422, 423 and 424 are electrically connected to, and controlled by, controller 408. These connections have also been omitted for the sake of clarity.

Resistors 415 and 416 bias the connections at load terminals 417 to a high voltage when switches 411 and 412 are turned off. In this manner, the load and the energy delivery circuit are brought to a common reference prior to delivering the multiphasic waveform. Additionally, the value of resistor 415 is chosen such that the current flowing through resistor 415 while energy is being delivered via load terminals 417 is minimal. For example, resistor 415 can be a 5000 ohm silicon coated power resistor. Preferably, the resistor 415 (or a corresponding resistor in any embodiment according to the present invention) has a resistance of 25,000 ohms or less, e.g., 10,000 ohms or less. In a preferred embodiment, the energy delivery device is a defibrillator for delivering a multiphasic waveform to a patient through load terminals 417. Since patient impedances are typically in the range between 25 ohms and 150 ohms, resistor 415 will receive only a small fraction of the total current flow.

Controller 408 selectively turns on and off switches 411, 412, 413 and 414 by activating turn-on circuits 421, 422, 423 and 424 respectively, to provide the truncated exponential multiphasic waveform to the patient through load terminals 417. For example, a first phase of the truncated exponential multiphasic waveform can be provided to the patient by selectively turning on switch 411 and switch 414 while keeping switch 412 and switch 413 off. In this manner, current will flow from energy storage device 401 through the drain-source junction of switch 411, through the patient via load terminals 417, through the drain-source junction of switch 414 and through resistor 420. A second phase of the truncated exponential multiphasic can be provided to the patient by selectively turning off switch 411 and switch 414 and turning on switch 412 and switch 413. In this manner, current will flow from energy storage device 401 through the drain-source junction of switch 412, through the patient via load terminals 417, through the drain-source junction of switch 413 and through resistor 420. Controller 408 senses the current flow through resistor 420 to ensure the correct amount of current is delivered to the patient. Accordingly, a multiphasic waveform is delivered to the patient through load terminals 417 by controlling the turn-on and turn-off of switches 411, 412, 413 and 414 in this manner. When controller 408 determines the correct amount of energy has been delivered to the patient, Controller 408 truncates the waveform by turning off whichever of switches 411, 412, 413 and 414 were on.

With regard to the connections of the disarm circuit, the first side of resistor 415 is electrically connected to the positive terminal of energy storage device 401 and a first side of resistor 453. The drain of switch 413 is electrically connected to a second side of resistor 415. The source of switch 413 is electrically connected to a first side of resistor 420 and to ground. The gate of switch 413 is electrically connected to a first side of resistor 429 and the cathode of diode 427. The drain of switch 426 is electrically connected to a second side of resistor 429. The gate of switch 426 is electrically connected to a first side of resistor 431 and an output of controller 408. The anode of diode 427 is electrically connected to the cathode of zener diode 428, the collector of switch 425 and a second side of resistor 453. The base of switch 425 is electrically connected to a first side of resistor 430 and a second side of resistor 431. The negative terminal of energy storage device 401 is electrically connected to the second side of resistor 420. The source of switch 426, the anode of zener diode 428, the emitter of switch 425 and a second side of resistor 430 are all electrically connected to ground.

Controller 408 deactivates the disarm circuit to allow energy to accumulate and be stored in energy storage device 401, and for energy delivery to the patient. Controller 408 turns on switch 412 via turn-on circuit 422 and switch 413 via turn-on circuit 423 to deliver one phase of the multiphasic waveform through load terminals 417 as previously discussed. In this case, diode 427 allows the drive signal from turn-on circuit 423 to be applied to the gate of switch 413 and block the drive signal from being shunted to ground through switch 425. Controller 408 deactivates the disarm circuit by providing an active signal to the first side of resistor 431 and the gate of switch 426. The active signal turns on switch 425 and switch 426. Switch 425 provides a current path through its collector-emitter junction for current flowing through resistor 453 so that voltage does not build on the gate of switch 413, causing unwanted turn-on. Zener diode 428 clamps the voltage at the collector of switch 425 to further limit the current flow through resistor 453 and switch 425. Switch 426 provides a current path through resistor 429 to shunt current at the gate of switch 413 to ground to eliminate nuisance turn-on of switch 413 due to current flow through resistor 453 and diode 427 due to the voltage clamped by zener diode 428.

Resistor 415 and switch 413 provide a path for current to flow to discharge or disarm energy storage device 401 without delivering energy through load terminals 417 and to minimize risk of injury to a user when servicing or transporting the energy delivery device. To activate the disarm circuit, controller 408 turns on switch 413 through turn-on circuit 423.

Temperature monitor 409 is electrically connected to controller 408 and senses the temperature of resistor 415, allowing controller to modulate the signal applied to activate or deactivate switch 425 and switch 426 in a manner similar to that described in U.S. Pat. No. 6,185,456 (the entirety of which is incorporated herein by reference). Accordingly, controller 408 can limit the current through resistor 415 during discharge by control of the disarm circuit when temperature monitor 409 senses that the temperature of resistor 415 has exceeded a predetermined threshold.

In addition, controller 408 can activate the disarm circuit to discharge energy in energy storage device 401 to a predetermined level based on patient requirements. For example, if energy storage device 401 is charged to a level in excess of the level required for the patient to be treated, controller 408 can activate the disarm circuit while monitoring energy remaining in the energy storage device 401 until the desired energy level is attained. When the desired energy level is attained, controller 408 deactivates the disarm circuit such that the defibrillator is ready to supply the multiphasic waveform to the patient through load terminals 417 at the correct energy level.

Additionally, the disarm circuit is activated when power has been removed from the unit but energy still exists in energy storage device 401. In order for the disarm circuit to operate when power has been removed from the energy delivery device, power is derived from the energy stored in energy storage device 401. Since controller 408 cannot apply an active signal to the first side of resistor 431 and the gate of switch 426 when power is removed from the energy delivery circuit, switch 425 and switch 426 function as in their respective off states. That is, no path exists for current to flow from energy storage device 401 through switch 425 or resistor 429 and switch 426 to ground. Current flowing from energy storage device 401 through resistor 453 and diode 427 turns on switch 413 to provide a discharge path from energy storage device 401 as previously discussed. Zener diode clamps the voltage at the collector of switch 425 to further limit the current flow through resistor 453 and thereby limit the voltage supplied to the gate of switch 413. Resistor 430 ensures switch 425 is turned off when the active signal is removed by shunting any stray current to ground. Accordingly, the disarm circuit of the present invention provides a path for current to flow from the energy storage device 401 through resistor 415 and the drain-source junction of switch 413 to ground with no system power and no interaction with controller 408. Therefore, in accordance with the disarm circuit of the present invention, the energy level in energy storage device 401 can be reduced to a safe level (e.g. around 20 volts) even after power has been removed from the energy delivery device.

In any of the above described methods of discharging energy from energy storage device 401 via the disarm circuit, current flows through resistor 415 which is incorporated into the energy delivery circuit. However, when the disarm circuit is inactive, resistor 415 conducts only minimal current due to the previously described difference in resistance values between resistor 415 and the load. Accordingly, unlike prior art disarm circuits where the dissipating resistor does not conduct current during application of the energy to the patient, resistor 415 is integrated into the energy delivery circuit so that it does conduct current when energy is delivered to the patient from energy storage device 401. However, the resistance of resistor 415 is selected such that the current flowing through resistor 415 has virtually no effect on the energy delivered to the patient.

Thus, the voltage stored in energy storage device 401 is controlled via controller 408 and the state of the power applied to the energy delivery device (power on or power off). Very few additional parts are required to perform both energy delivery to the load and to safely discharge or disarm energy storage device 401 as the disarm circuit is integrated into the energy delivery circuit. This lower part count contributes to a simpler circuit design and improved reliability.

Figure 5:
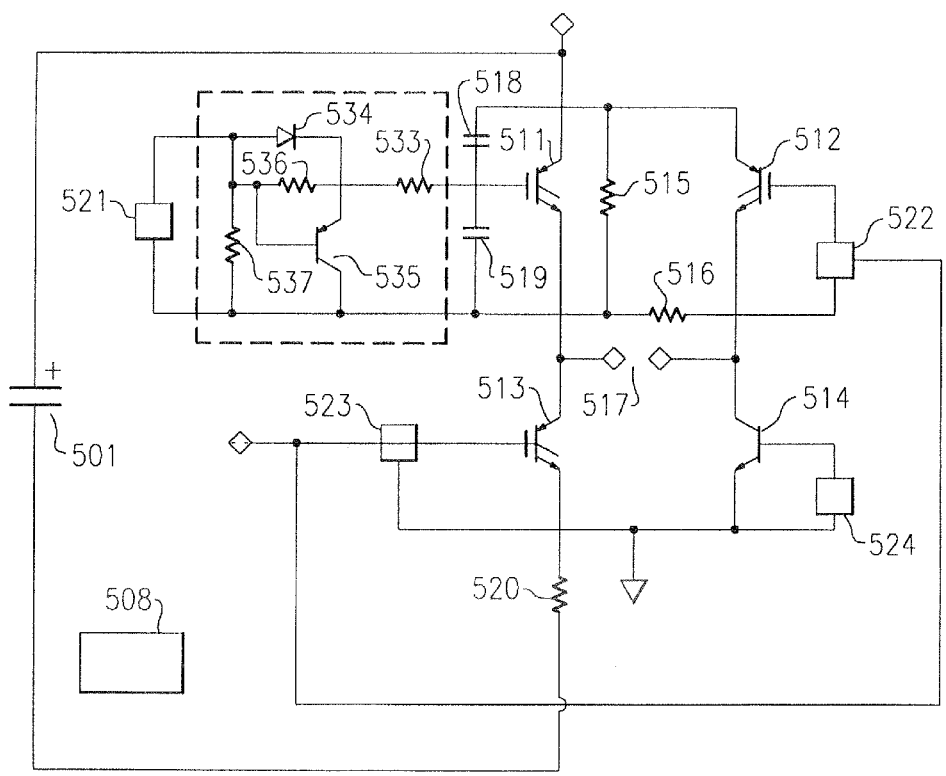
FIG. 5 is a schematic diagram of an embodiment of an energy delivery circuit including a shoot-through elimination circuit in accordance with the present invention.

Referring to FIG. 5, a multiphasic defibrillator circuit including an energy delivery circuit and a shoot-through elimination circuit in accordance with the present invention is shown where components analogous to components in FIG. 4 have been provided with reference numbers in which the last two numbers are the same as the last two numbers in the reference numbers of the respective analogous components in FIG. 4 (e.g., 501 in FIG. 5 is analogous to 401 in FIG. 4). The energy delivery circuit includes energy storage device 501, controller 508, switches 511, 512, 513 and 514, resistors 515, 516 and 520, turn-on circuits 521, 522, 523 and 524 and load terminals 517. The configuration and operation of the energy delivery circuit correspond to those discussed in detail with reference to FIG. 4.

Rapid turn-on of switch 513 can cause a high dv/dt at the source of switch 511. Parasitic capacitances, represented by capacitor 518 and capacitor 519, form a capacitive voltage divider network that can result in the build-up of voltage on the gate of switch 511 due to the high dv/dt and cause a nuisance turn-on of switch 511 while switch 513 is on. As can be seen in FIG. 5, turning on switch 511 while switch 513 is conducting would create a shoot-through path to ground for the energy stored in energy storage device 501, which would likely result in damage to the energy delivery device.

A shoot-through elimination circuit is provided which includes switch 535, diode 534 and resistors 533, 536 and 537. In the present embodiment, switch 535 is a pnp transistor and diode 534 is any diode capable of providing a current path from turn-on circuit 521 to the gate of switch 511 while providing a voltage clamp across the emitter base junction of switch 535 (IN4148 for example).

With regard to the connections of the shoot-through elimination circuit, the gate of switch 511 is electrically connected to a first side of resistor 533. The emitter of switch 535 is electrically connected to a second side of resistor 533, a first side of resistor 536 and the cathode of diode 534. The base of switch 535 is electrically connected to a second side of resistor 536, a first side of resistor 537 the anode of diode 534 and a first terminal of turn-on circuit 521. The collector of switch 535 is electrically connected to a second side of resistor 537 and a second terminal of turn-on circuit 521.

Resistors 533, 536 and 537 provide a current flow path to activate the shoot-through elimination circuit as voltage builds up on the gate of switch 511. For example, when voltage starts to accumulate on the gate of switch 511 due to the rapid turn-on of switch 513 and parasitic capacitances 518 and 519, current begins to flow through resistors 533, 536 and 537. This current flow turns on switch 535, which shunts the voltage away from the gate of switch 511 through resistor 533. Therefore, the shoot-through elimination circuit of the present invention is in the form of a shunt circuit. This shunt circuit provides a low impedance path for the dv/dt at the gate of switch 511 during high speed turn-on of switch 513. Thereby, the shoot-through elimination circuit in accordance with the present invention eliminates nuisance turn-on of switch 511 and subsequent shoot-through current flow through switch 511 and switch 513.

To deliver at least one of the phases of the multiphasic waveform to the patient, controller 508 turns on switch 511 via turn-on circuit 521 and switch 514 via turn-on circuit 524. Diode 534 provides a current path from turn-on circuit 521 through resistor 533 to the gate of switch 511 while providing a voltage clamp across the emitter base junction of switch 535, keeping the shunt circuit of the shoot-through elimination circuit off while switch 511 is being intentionally activated.

The shoot-through anomaly and shoot-through elimination circuit have been described in detail with regard to switches 511 and 513. However the shoot-through anomaly caused by the rapid turn on of switch 513 and the parasitic capacitances at the gate of switch 511 occur with respect to switch 514 and switch 512 as well. For example, the rapid turn on of switch 514 could cause a high dv/dt at the source of switch 512. Parasitic capacitances at the gate of switch 512 (not shown) would form a capacitive voltage divider network that can result in the build-up of voltage on the gate of switch 512, causing nuisance turn-on of switch 512 while switch 514 is conducting. Again, as can be seen in FIG. 5, turning on switch 512 while switch 514 is conducting would create a shoot-through path to ground for the energy stored in energy storage device 501 which would likely result in damage to the energy delivery device. A shoot-through elimination circuit in accordance with the present invention can be incorporated on both sides of the energy delivery circuit to completely eliminate the shoot-through anomaly.

Figure 6:
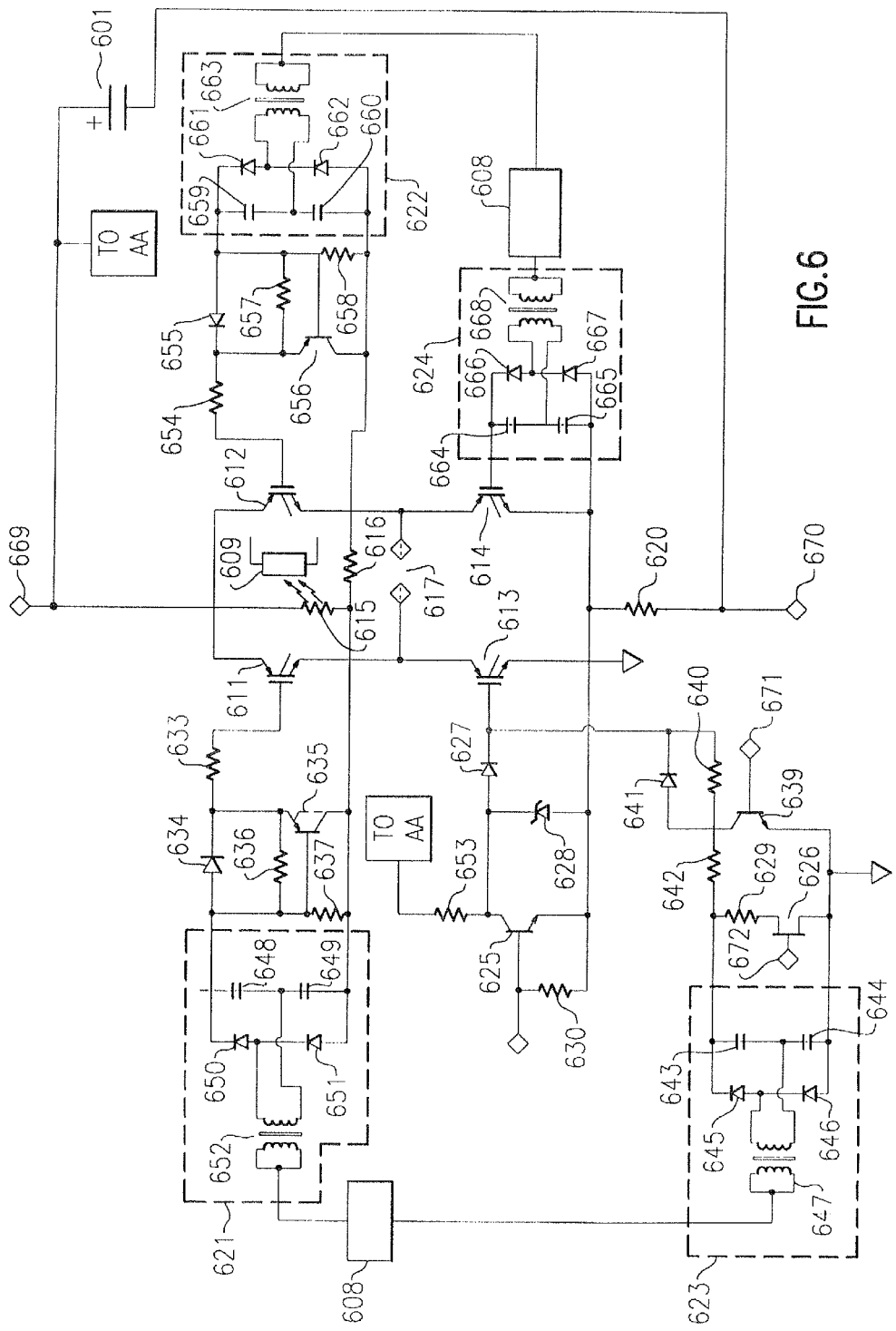
FIG. 6 is a schematic diagram of an embodiment of an energy output circuit including a disarm circuit and a shoot-through elimination circuit in accordance with the present invention.

FIG. 6 is a schematic drawing of an embodiment of an H-Bridge energy delivery circuit including a disarm circuit and shoot-through elimination circuits in accordance with the present invention, where components analogous to components in FIG. 4 have been provided with reference numbers in which the last two numbers are the same as the last two numbers in the reference numbers of the respective analogous components in FIG. 4 (e.g., 601 in FIG. 6 is analogous to 401 in FIG. 4). As can be seen, a second shoot-through elimination circuit has been included on the opposite side of the H-Bridge energy delivery circuit to completely eliminate the shoot-through anomaly and reduce the risk of damage to all of the switches of the H-Bridge energy delivery circuit.

The H-Bridge energy delivery circuit includes energy storage device 601, controller 608 (shown in two places), switches 611, 612, 613 and 614, resistors 615, 616 and 620, turn-on circuits 621, 622, 623 and 624, and load terminals 617.

Turn-on circuit 621 consists of capacitors 648 and 649, diodes 650 and 651 and transformer 652. Turn-on circuit 622 consists of capacitors 659 and 660, diodes 661 and 662 and transformer 663. Turn-on circuit 623 consists of capacitors 643 and 644, diodes 645 and 646 and transformer 647. Turn-on circuit 624 consists of capacitors 664 and 665, diodes 666 and 667 and transformer 668. Transformers 647, 652, 663 and 668 isolate controller 608 from the high energy in the H-Bridge energy delivery circuit and contribute to the rectification of the drive signals. Diodes 650 and 651 and capacitors 648 and 649 of turn-on circuit 621 form a voltage doubling and rectification circuit to further rectify the drive signal and provide the required voltage level at the gate of switch 611. Diodes 661 and 662 and capacitors 659 and 650, diodes 645 and 646 and capacitors 643 and 644, and diodes 666 and 667 and capacitors 664 and 665 perform smilar voltage doubling and rectification functions for appropriate turn-on voltage at the gates of switches 612, 613 and 614, respectively. The configuration and operation of the H-Bridge energy delivery circuit have been discussed in detail with reference to FIG. 4 and will not be repeated here.

The disarm circuit includes switches 613, 625 and 626, resistors 615, 629, 630, and 653, diode 627, zener diode 628 and temperature monitor 609. The configuration and operation of the disarm circuit have been discussed in detail with reference to FIG. 4 and will not be repeated here.

The first shoot-through elimination circuit includes switch 635, diode 634 and resistors 633, 636 and 637. The second shoot-through elimination circuit includes switch 656, diode 655 and resistors 654, 657 and 658. The configuration and operation of these shoot-through elimination circuits are as discussed in detail with reference to FIG. 5 and will not be repeated here. However, capacitors 650 and 651 and capacitors 659 and 660, in addition to the voltage doubling and rectification functions previously discussed, work in conjunction with the first and second shoot-through elimination circuits respectively to improve the response time of the shoot-through elimination circuit. With respect to the first shoot-through elimination circuit, for example, as a voltage builds at the gate of switch 611 due to the high dv/dt when switch 613 is rapidly turned on as previously discussed, current begins to flow through resistors 633, 636 and 637. However, during a high dv/dt, capacitors 648 and 649 which are electrically connected in parallel with resistor 637 will initially appear as a short circuit, and shunt current away from resistor 637 to cause a faster turn-on of switch 635. This faster response time allows larger resistance values to be used for resistors 636 and 637, which in turn decreases the drive current requirements for turn-on circuit 621.

Connection points 669, 670, 671 and 672 are connections to controller 608 for monitoring and/or control purposes.

In addition, the embodiment shown in FIG. 6 includes switch 639, diode 641 and resistor 640. Diode 641 bypasses resistor 640 for voltages supplied to the gate of switch 613 by turn-on circuit 623 during delivery of the multiphasic waveform. Controller 608 monitors current levels at connection points 669 and 670 during discharge and disarm operations and turns on switch 639 if current levels exceed a predetermined value. When switch 639 is turned on, voltage at the gate of switch 613 is shunted to ground through resistor 640, keeping switch 613 in the off state. Resistor 640 and diode 641 slow the turn off of switch 613 when switch 639 is turned on to eliminate ringing of the paddles at load terminals 617.

Figure 7:
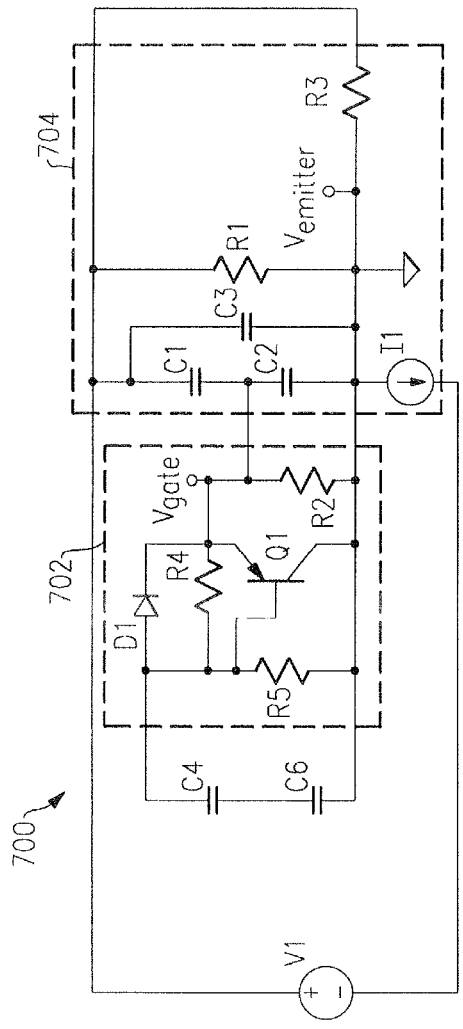
FIG. 7 is a SPICE circuit diagram modeling an embodiment of a shoot-through elimination circuit and high energy switch in accordance with the present invention.

Referring now to FIG. 7, a Simulation Program With Integrated Circuit Emphasis (SPICE) simulation circuit 700, modeling a shoot-through elimination circuit 702 and a switch 704, is shown. The switch 704 simulates an IGBT, for example, switch 511 (see FIG. 5). The components illustrated within the circuit 702 are the same as, and model the performance of, those described for the shoot-through elimination circuit shown in FIG. 5, and will not be described in detail here. In addition, capacitors C1, C2, and C3 within switch 704 model the parasitic capacitances of a high voltage switch. As is known in the art, the SPICE program simulates the performance of the circuit 700 and presents the results of the simulation to a user. For instance, the voltage response at the gate of switch 704 may be simulated and presented to a user.

Figure 8:
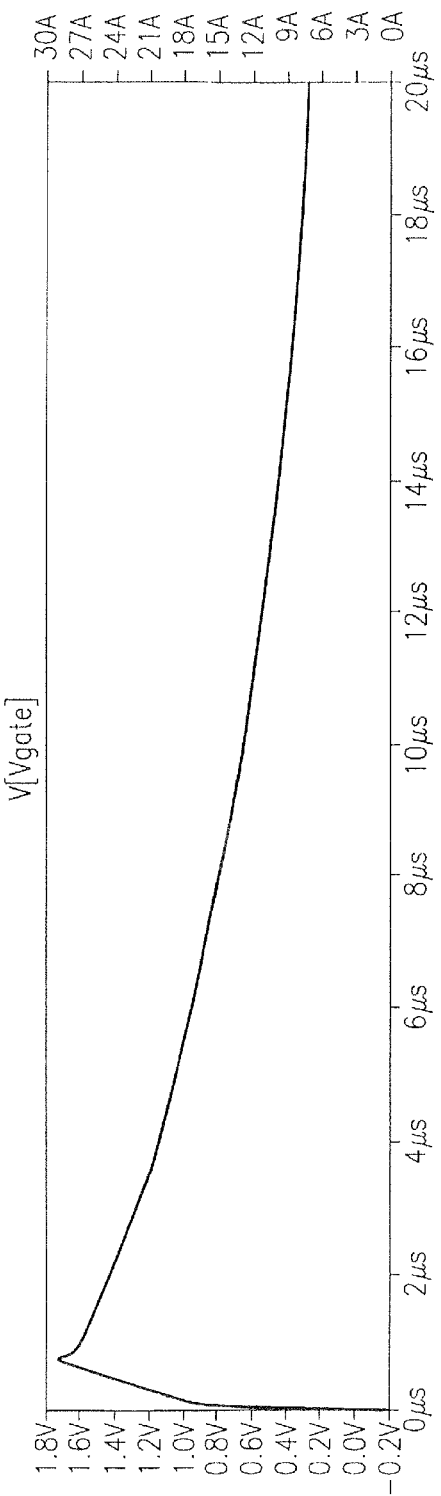
FIG. 8 is a SPICE simulation of the voltage waveform at the gate of the switch of FIG. 7.

Referring now to FIG. 8, the voltage waveform present on the gate of switch 704 according to a SPICE simulation of the circuit 700 is illustrated. This waveform shows the voltage at the gate of the switch 704 is capped at a maximum of approximately 1.6 volts due to the shoot-through elimination circuit. Since 1.6 volts is within the operating region of most switches, no damage occurs to switch 704.

Figure 1:
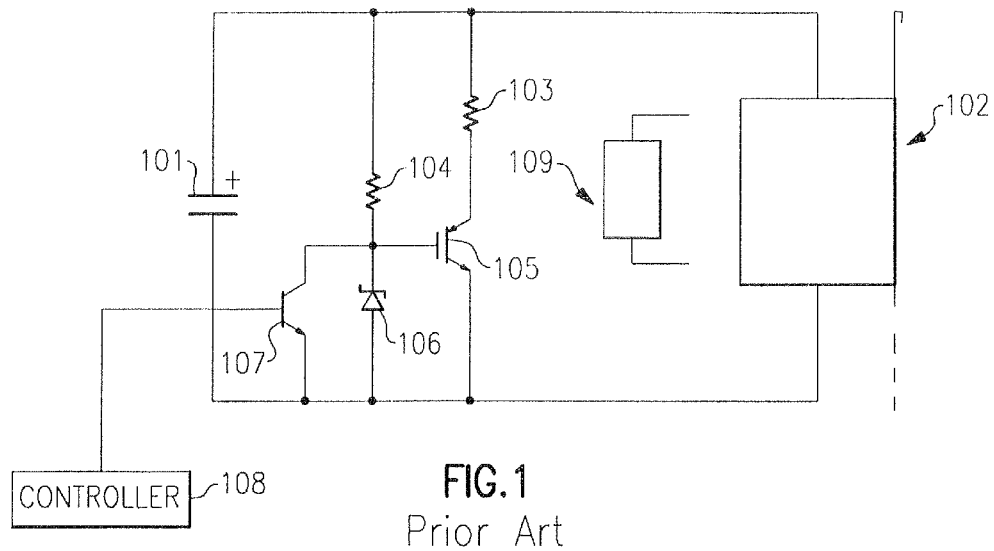
FIG. 1 is a schematic diagram of a prior art energy discharging circuit.
Figure 2:
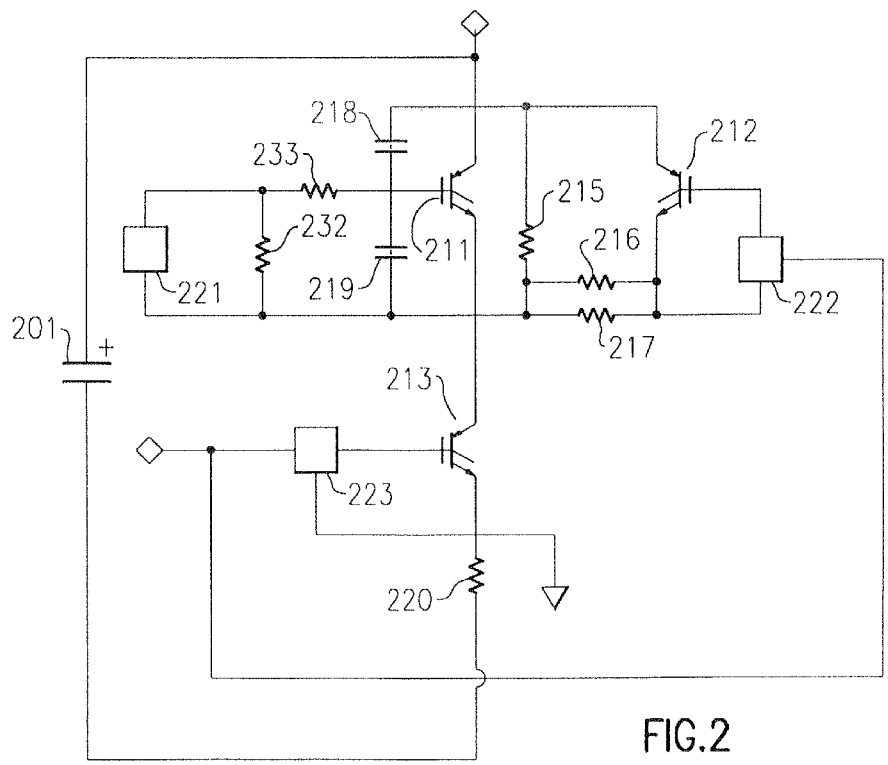
FIG. 2 is a schematic diagram of a prior art defibrillator output circuit.
Figure 9:
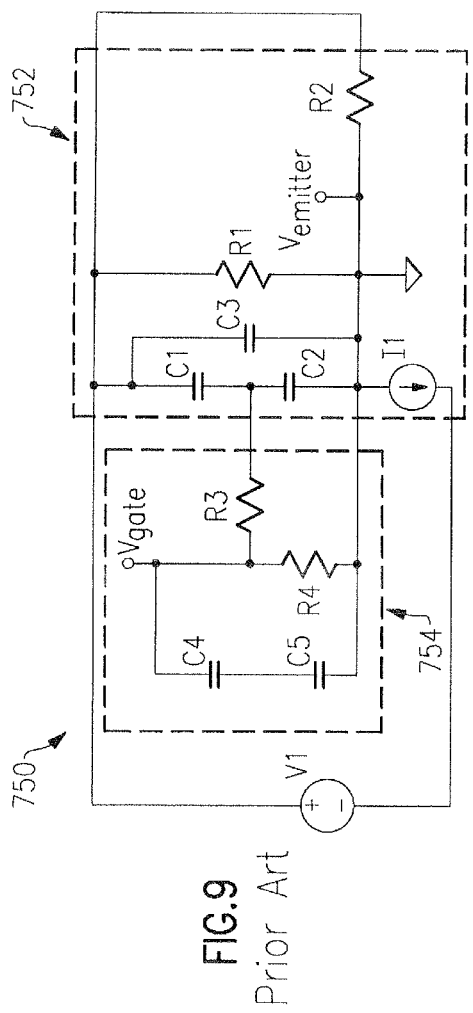
FIG. 9 is a SPICE circuit diagram of a prior art device including a high energy switch.

Referring now to FIG. 9, a SPICE simulation circuit 750, modeling a switch 752 and circuit components 754 according to prior art systems, is shown. Switch 752 simulates an IGBT, for example, switch 211 (see FIG. 2). The circuit components 754 correspond to those described with respect to FIG. 2, and they will not be described here. As can be seen, the prior circuit 750 does not include a shoot-through current elimination circuit in accordance with the present invention.

Figure 10:
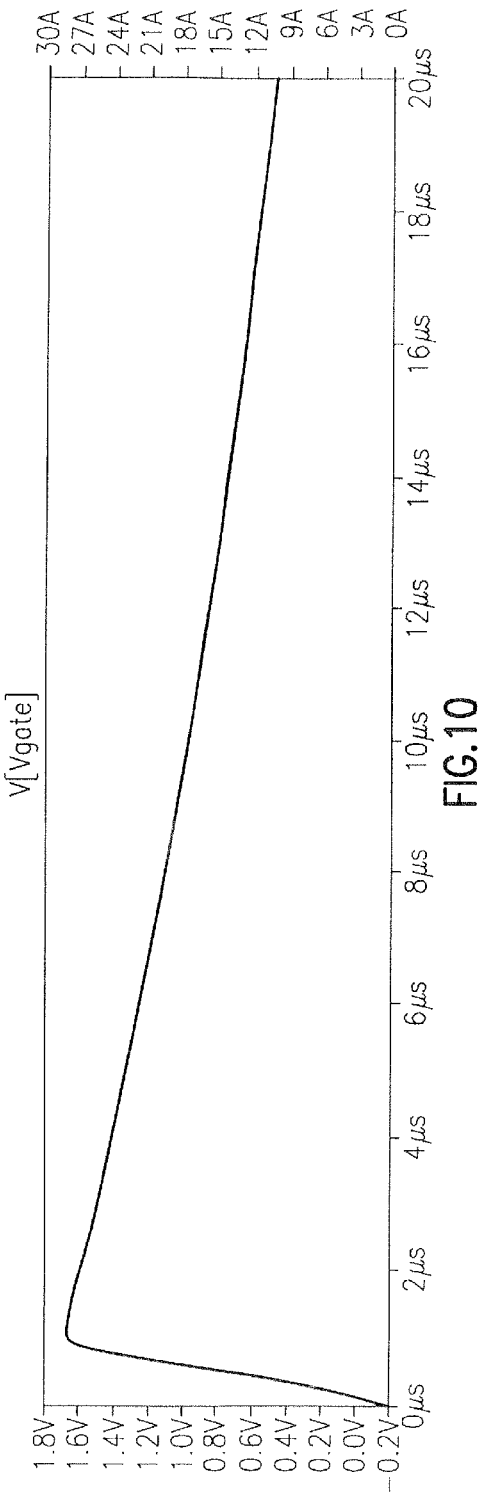
FIG. 10 is a SPICE simulation of the voltage waveform at the gate of the switch of FIG. 9.

Referring now to FIG. 10, the voltage waveform present on the gate of switch 752 according to a SPICE simulation of the circuit 750 is illustrated. This waveform shows the voltage at the gate of the switch 752 exceeds 1.6 volts, and, in fact, peaks at a much higher value of around 10 volts due to the absence of a shoot-through elimination circuit. Thus, it is likely that switch 752 will be turned on, providing a direct path to ground and causing a short circuit.

An embodiment of a compact defibrillator unit 800 which includes a disarm circuit and a shoot-through elimination circuit in accordance with the present invention is shown in FIGS. 11-16. In addition to conserving space by way of the integration of the disarm circuit with the energy delivery circuit as previously described, defibrillator unit 800 also employs a detachable electrical connection that serves to electrically connect capacitor bank 802 with energy delivery circuit 806 when defibrillator unit 800 is assembled. As a result, defibrillator unit 800 is of a very compact volume so that it is easy to use and transport while still being able to generate the desired energy level and pulse duration for the defibrillation function. To generate the desired energy level and pulse duration, defibrillator unit 800 includes an energy storage device in the form of a bank of capacitors 802 that are maximized in their capacitance rating for the size of defibrillator unit 800 and the desired defibrillation waveform.

More particularly, defibrillator unit 800 includes clam shell housing halves including upper housing member 808 and lower housing member 810 that cooperate to form a compact, portable housing for defibrillator unit 800 when assembled. The housing volume is preferably less than 140 cubic inches and more preferably approximately 130 cubic inches, which is significantly lower than has been achieved in prior art commercial defibrillator units, particularly those that provide energy pulses having a multiphasic, low-tilt waveform.

Figure 11:
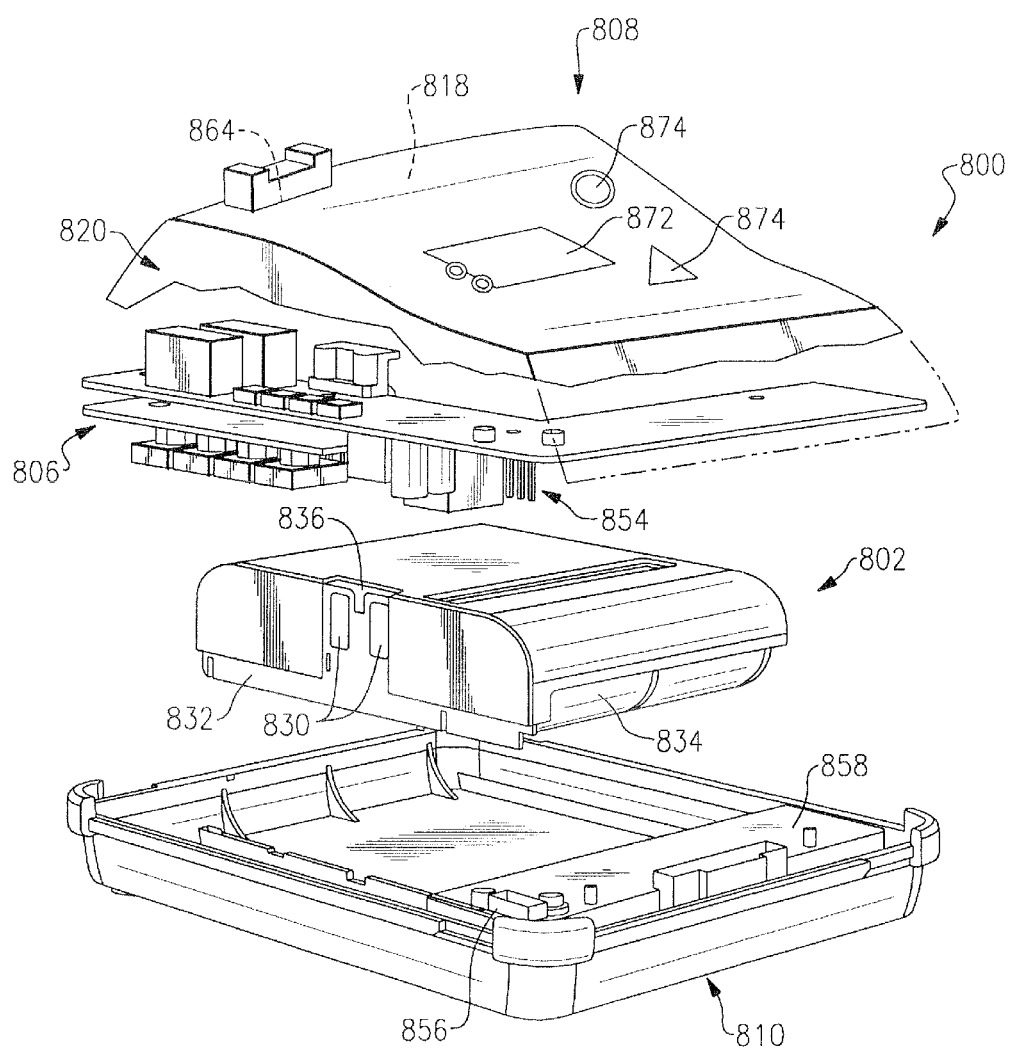
FIG. 11 is an exploded, perspective view of an embodiment of a defibrillator unit in accordance with the present invention showing an upper housing member and a lower housing member with circuitry for the unit on a printed circuit board assembly and a bank of capacitors for energy storage.
Figure 12:
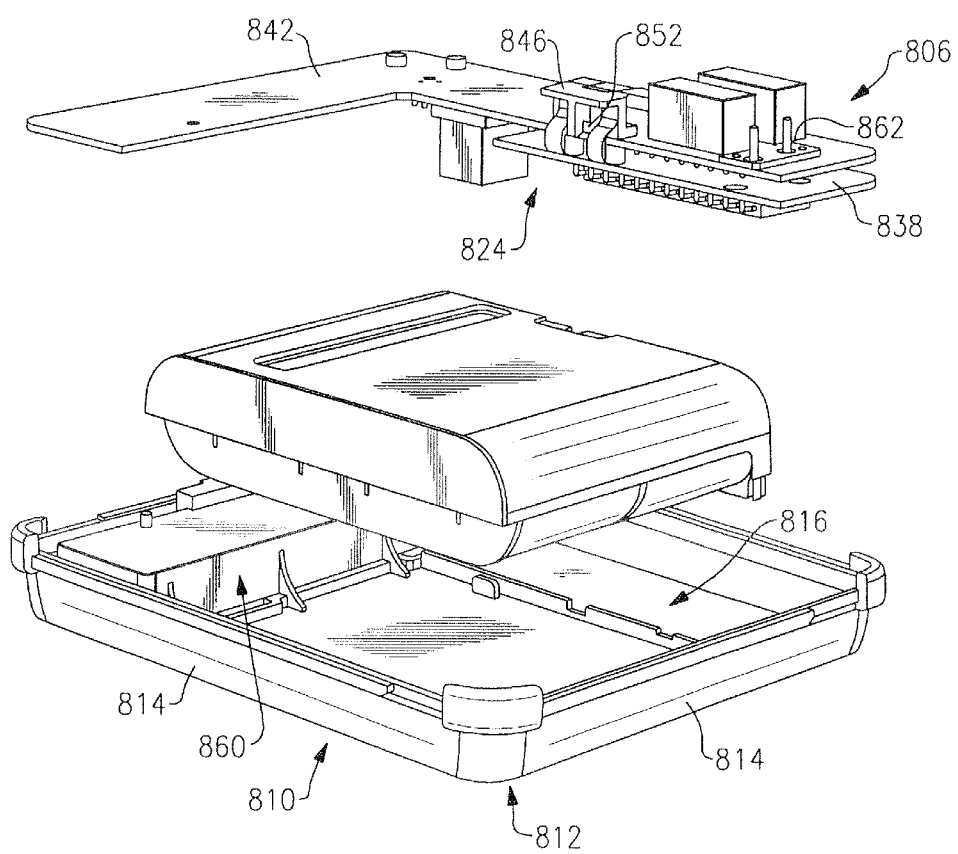
FIG. 12 is an exploded, perspective view of the lower housing member, the capacitor bank, the circuit board assembly, and a wireless, detachable electrical connection between the capacitor bank and circuit board assembly of the embodiment depicted in FIG. 11.
Figure 15:
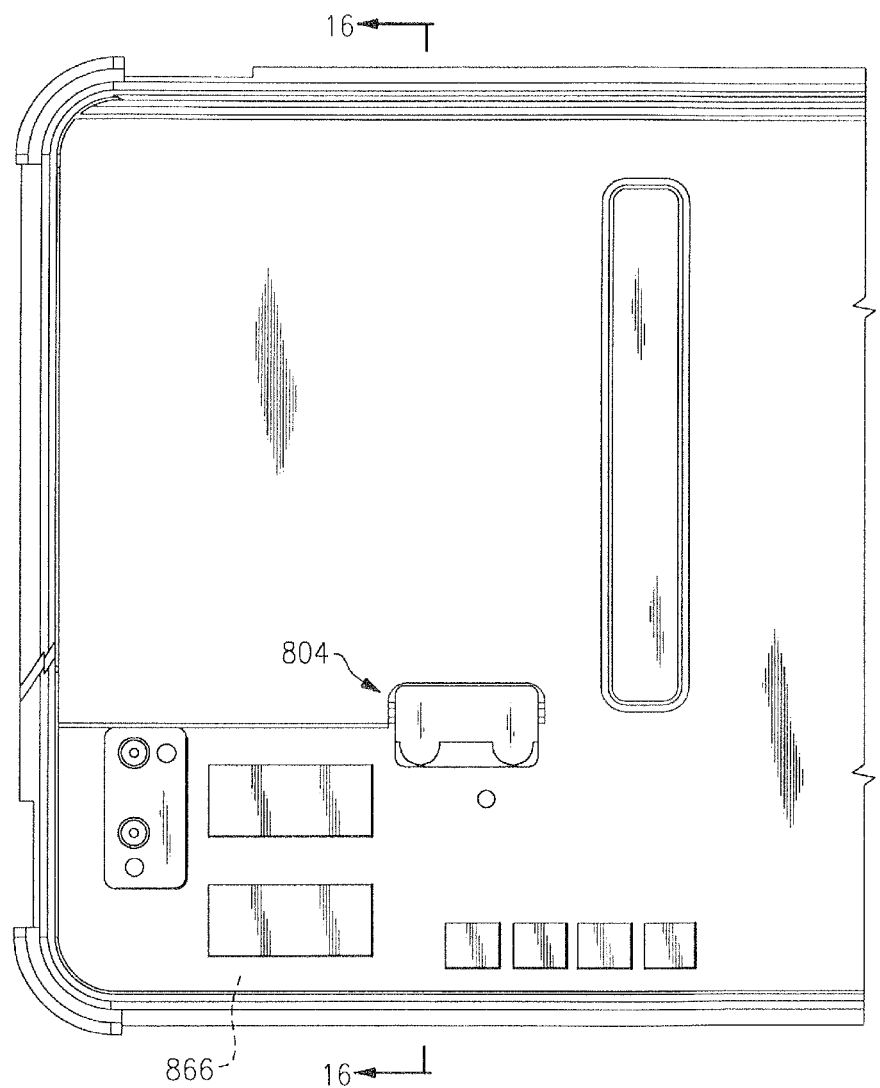
FIG. 15 is a plan view of the lower housing member including the capacitor bank, and the circuit board assembly, shown partially in cut-out, disposed thereover, of the embodiment depicted in FIG. 11.
Figure 16:
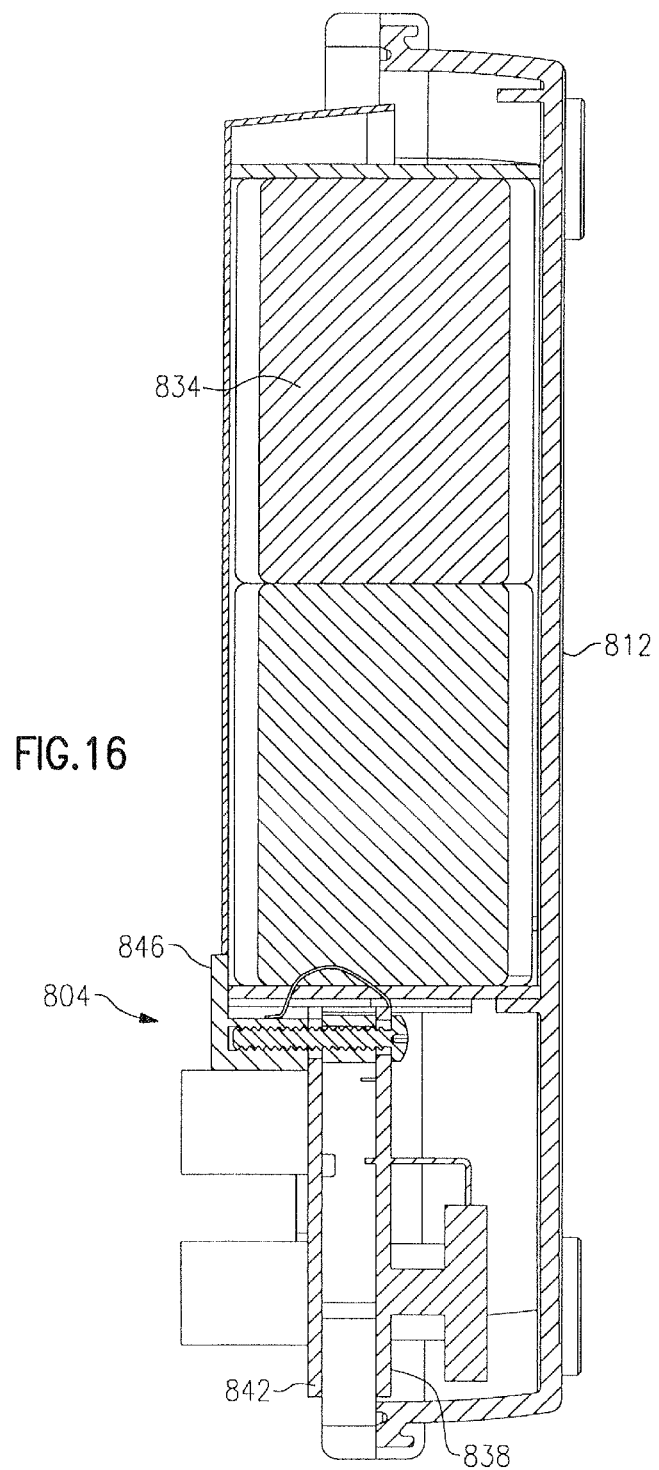
FIG. 16 is a cross sectional view taken along line 16-16 of FIG. 15, showing the detachable electrical connection between the circuit board assembly and the capacitor bank.

As shown in FIG. 12, lower housing member 810 includes base wall 812 and upstanding sidewalls 814 that form internal space 816 for carrying the capacitor bank 802 therein. Similarly, as shown in FIGS. 11 and 13, upper housing member 808 includes upper wall 818 and depending sidewalls 820 which cooperate to form internal space 822 in which energy delivery circuit PCB (printed circuit board) assembly 824 is carried. The upper housing member 808 is shown in FIG. 11, which is a cut-out view in order to also show the energy delivery circuit PCB assembly 824.

In the embodiment shown in FIG. 11, a detachable slide connection made between contacts of capacitor bank 802 and energy delivery circuit 806 (namely, between leaf spring metallic strip 828 of the energy delivery circuit 806 and metallic strips 830 of the capacitor bank 802, as described in more detail below). In this manner, the electrical connection between capacitor bank 802 and energy delivery circuit 806 is made when clamshell housing halves 808 and 810 are assembled together. Accordingly, the electrical connection between capacitor bank 802 and energy delivery circuit 806 is broken when clamshell housing halves 808 and 810 are disassembled.

In prior defibrillator units, the energy storage device and the energy delivery circuit have been interconnected via high voltage wiring, which has resulted in relatively large space requirements. These high voltage wires were relatively large as they required multiple layers of insulation to meet safety and FDA requirements as otherwise the high voltage they carry could reach the battery contacts in the unit potentially shocking users. In addition, the high voltage wires were crimped to their contact connections so that they were cumbersome to assemble and prone to manufacturing defects and wear over time.

With the detachable connection, the high voltage wiring present in prior art units is not required. Accordingly, defibrillator unit 800 realizes significant space savings in the internal space thereof, allowing it to be more compact than prior art defibrillator units, not necessarily reducing the size of energy storage device 802. In this manner, the defibrillator unit 800 in accordance with the present invention also allows the voltage level for energy delivery circuit 806 to be kept to a minimum, e.g., about 1300 volts, while still delivering low-tilt, multiphasic energy pulses of an optimum duration to patients.

To provide a secure high voltage connection, the contacts of capacitor bank 802 and energy delivery circuit 806 are resiliently engaged against each other so that they are biased together. In a preferred and illustrated form, the contacts for energy delivery circuit 806 include a pair of arcuately configured leaf spring metallic strips 828, and the contacts for capacitor bank 802 include a pair of corresponding flat, metallic strips 830. Flat metallic strips 830 are provided on circuit board 832 to which individual capacitors 834 of capacitor bank 802 are electrically connected. Flat metallic strips 830 are arranged on either side of notch 836 formed in the upper edge of circuit board 832. Leaf spring contacts 828 are fixed to lower board 838 of PCB assembly 824 at their bottom ends. Guide cam member 840 (FIG. 14) is secured to upper board 842 of PCB assembly 824, and is of non-conductive material, e.g., plastic. Guide cam member 840 includes a pair of guide channels 844 in which free, upper ends of leaf spring contacts 828 reside. As upper housing member 808 including PCB assembly 824 secured therein is moved toward lower housing member 810, the arcuate portions of leaf spring contacts 828 resiliently engage flat metallic strips 830 so that the arcuate portions of leaf spring contacts 828 are pushed toward a flat configuration with the upper free ends thereof riding up guide channels 844.

Guide cam member 840 includes an upper wall 846 extending transverse to the guide channels 844 in a direction parallel to capacitor bank 802. Upper wall 846 limits upward travel of the upper free ends of leaf spring contacts 828 in their respective channels 844. A centrally oriented cam projection 848 transversely depends from the outer edge of the upper wall 846 generally aligned between leaf spring contacts 828, and generally in alignment with notch 836 of PCB 832 for assembly and alignment purposes. Projection 848 includes inwardly facing cam surface 850 disposed below a recessed cutout 852 in projection 848. Upper wall 846 extends sufficiently outward to an extent that projection 848, and specifically cam surface 850 thereof, engages PCB 832 in notch 836. Projection 848 terminates at its lower end above the fixed lower ends of leaf spring contacts 828.

Accordingly, when upper housing member 808 and lower housing member 810 are shifted toward each other to bring the upper edges of their respective side walls into engagement for assembly, leaf spring contacts 828 will initially engage flat metallic strips 830 causing upward shifting of their respective free ends in guide channels 844. Continued shifting of upper and lower housing members 808 and 810 toward each other brings cam surface 850 into engagement with the base of notch 836 and butting against the back of PCB 832. In this manner, cam surface 850 pushes leaf spring contacts 828 and flat metallic strips 830 into a tight engagement with each other against the bias provided by the arcuate portions of leaf spring contacts 828. With housing members 808 and 810 fully assembled, the base of notch 836 will be in confronting relation with the base of recessed cutout 852, and the free ends of leaf spring contacts 828 will be close to or abutting upper wall 846 of guide member 840. At this time, fasteners can be employed to keep housing members 808 and 810 assembled together.

To disconnect capacitor bank 802 from energy delivery circuit 806 to disassemble defibrillator unit 800 for servicing, for example, housing members 808 and 810 are unfastened and shifted away from each other. In this instance, cam surface 850 will disengage from the back of capacitor PCB 832, and leaf spring contacts 828 will resiliently ride against flat metallic strips 830 until disengaged therefrom, thus breaking the electrical connection between capacitor bank 802 and energy delivery circuit 806.

As is apparent, the above-described detachable connection provides a slide connection between capacitor bank 802 and energy delivery circuit 806 that is both secure and simple in terms of providing proper assembly and disassembly. Accordingly, large high voltage wires are eliminated and the aforementioned effort required for making the electrical crimp connections and errors due to incorrect wiring are mitigated.

In addition to the space savings achieved by the integral disarm circuit and detachable electrical connection, other enhancements have been provided which contribute to minimizing the housing volume. For example, both the battery contacts and patient contacts have been incorporated in terminal pins provided on PCB assembly 824. In this manner, wiring between the PCBs and the patient electrode cables and batteries has been eliminated.

More specifically, the battery contacts include a set of terminal pins 854 projecting downwardly from board 842. A slot opening 856 is formed in base wall 858 of battery compartment 860 in lower housing member 810. When upper and lower housing members 808 and 810 are assembled, pins 854 project directly into battery compartment 860 through slot opening 856 where they are connected to the battery power source for the defibrillator unit 800.

Similarly, the patient contacts are integrated onto the PCB assembly, and specifically upper board 842 via a pair of terminal pins 862 projecting upwardly therefrom. Pins 862 are aligned with well 864 integral with upper housing member 808. When upper and lower housing members 808 and 810 are assembled, pins 862 extend in through openings 866 formed in well 864 so as to project externally of the internal housing space recessed relatively low in well 864. The free ends of the cables for the patient electrodes include a common socket having a female configuration into which pins 862 can be plugged. Accordingly, a defibrillator unit 800 in accordance with the present invention eliminates wiring extending between the respective upper and lower housing halves 808 and 810 and, in particular, electrical components installed therein.

Upper wall 818 of upper housing member 808 is preferably inclined from front to back so that it is lowest at the front end of defibrillator unit 800 and higher toward the back end of defibrillator unit 800. Additionally upper wall 818 includes cutout 872 for viewing the LCD display. As the user interface is primarily incorporated in upper wall 818, the incline of wall 818 allows display text to be read easier and controls to be more easily used. With the exemplary dimensions previously discussed, the height dimension can be approximately two inches at the front (thinnest portion) of the housing and approximately three inches at the rear (thickest portion) of the housing due to the inclination of housing upper wall 818.

As previously mentioned, PCB assembly 824 includes energy delivery circuit 806, which preferably has an H-bridge configuration, as has been previously described. Accordingly, lower PC board 838 includes four IGBTs 866 mounted thereto. In addition to PC Boards 838 and 842, a main PC Board is mounted proximate the interior surface of upper wall 818 and includes a microprocessor, power supply, preamp, and optionally a speech unit mounted thereto. In addition, main PC Board 868 mounts LCD display 870 and user interface controls 874.

The space savings generated by the detachable connection described herein further provides a reduction in housing volume, and in particular with respect to the internal spaces 816 and 822 of the housing members 808 and 810, respectively. In practice, a housing volume of approximately 133 cubic inches has been achieved. By way of example and not limitation, the box-like housing can have a length dimension of approximately eight inches, a width dimension of approximately seven inches and height dimension in the range of approximately two inches to approximately three inches. At the same time, the space savings also allows the capacitor bank 802 to still be relatively large for adequately delivering the multiphasic energy to the patient. In practice, a capacitor bank of approximately 300 microfarads has been achieved. Accordingly, the present defibrillator unit 800 can generate multiphasic waveforms that are at a low tilt, as the amount of stored energy is relatively high in the unit. At the same time, the voltage developed for the discharge circuit can be kept to a minimum, as there is sufficient energy stored to enable delivery of multiple phases of the energy pulse.

Figure 17:
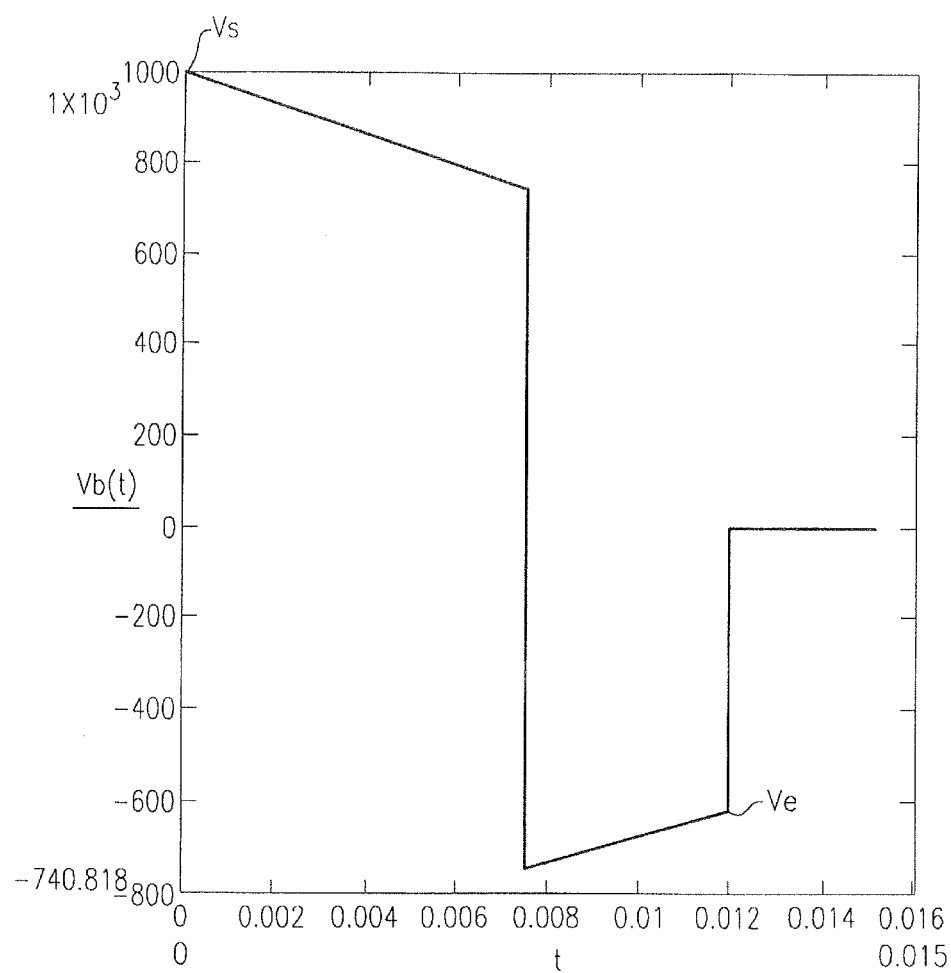
FIG. 17 is a graph of a representative example of a low-tilt 150 Joule pulse.

FIG. 17 shows an example of a multiphasic, low tilt waveform that can be achieved by a compact defibrillator of the present invention. The tilt of the waveform is defined as:

$$(Vs-Ve)/Vs*100 = \text{Tilt in Percent}$$

where:
Vs is the starting voltage
Ve is the ending voltage.

A lower tilt of the waveform provides a higher terminating current, which is more effective in preventing post shock arrhythmias. In a preferred embodiment, the tilt is less than 50 percent. In the present embodiment, the tilt is approximately 40 percent. Capacitance values of greater than 250 microfarads, are known to provide a lower tilt waveform, and can provide for lower current defibrillation. In the present embodiment, the bank of capacitors 802 has a capacitance value greater than 300 microfarads.

The present invention as described herein is applicable not only to defibrillator units but also to other applications of energy delivery devices, particularly H-Bridge energy delivery devices, such as powering of electric motors for example.

Any two or more structural parts of the devices described herein can be integrated. Any structural part of the devices described herein can be provided in two or more parts, which may be held together, if necessary or desired. Similarly, any two or more functions can be conducted simultaneously, and/or any function can be conducted in a series of steps.

The invention claimed is:

1. A device comprising:
an energy storage device;
an energy discharge circuit operably coupled to the energy storage device, the energy discharge circuit being operable to deliver energy from the energy storage device to a patient by at least one switch included in the energy discharge circuit, the at least one switch being controlled by a controller,
wherein the discharge circuit form an H-bridge circuit comprising four delivery switches which are operable to deliver at least one energy pulse, the at least one switch being one of said four delivery switches; and a disarm circuit also including the at least one switch, the disarm circuit being operable to prevent energy from being delivered to the patient when the disarm circuit is activated.

2. The device of claim 1, wherein activation of the disarm circuit activates the at least one switch.

3. The device of claim 1, wherein the disarm circuit electrically disconnects the energy storage device from the discharge circuit.

4. The device of claim 1, wherein energy stored in the energy storage device is discharged to ground upon activation of the disarm circuit.

5. The device of claim 1, wherein the controller monitors the amount of energy stored in said energy storage device and activates the disarm circuit to regulate the amount of energy stored in said energy storage device.

6. The device of claim 1, wherein said controller deactivates the disarm circuit to store energy in the energy storage device.

7. The device of claim 1, wherein the at least one switch activates when power to the controller is removed.

8. The device in claim 1, wherein the discharge circuit is configured to delivery energy in the form of a multiphasic wave-form.

9. The device of claim 1, wherein the disarm circuit automatically discharges energy from said energy storage device when a level of stored energy in the energy storage device exceeds a predetermined energy level.

10. A method for regulating stored energy, the method comprising:
 determining, based on a monitored energy storage level, whether to discharge at least a portion of the stored energy;
 selectively activating a disarm circuit including at least one switch based on the discharge determination, the at least one switch also being included in a discharge circuit; and
 adjusting at least a portion of the stored energy by the disarm circuit.

11. The method of claim 10, wherein activation of the disarm circuit activates the at least one switch.

12. The method of claim 10, wherein adjusting at least a portion of the stored energy includes discharging the stored energy to ground when the disarm circuit is activated.

13. The method of claim 10, wherein determining whether to discharge a least a portion of the energy includes determining if an amount of energy stored in the energy storage device exceeds a desired level.

\* \* \* \* \*